United States Patent [19]
Marraccini et al.

[11] Patent Number: 5,877,357
[45] Date of Patent: Mar. 2, 1999

[54] PROCESS FOR PREPARING PERHALOETHERS FROM PERHALOOLEFINS AND NEW PERHALOETHERS THEREBY OBTAINED

[75] Inventors: Antonio Marraccini; Antonio Pasquale; Tiziana Fiorani, all of Novara; Walter Navarrini, Milan, all of Italy

[73] Assignee: Ausimont S.p.A., Milan, Italy

[21] Appl. No.: 826,728

[22] Filed: Apr. 7, 1997

Related U.S. Application Data

[62] Division of Ser. No. 352,440, Dec. 9, 1994, Pat. No. 5,648,560, which is a continuation of Ser. No. 283,614, Aug. 1, 1994, abandoned, which is a continuation of Ser. No. 38,188, Mar. 29, 1993, abandoned, which is a continuation of Ser. No. 722,408, Jun. 20, 1991, abandoned, which is a continuation-in-part of Ser. No. 540,639, Jun. 19, 1990, abandoned.

[30] Foreign Application Priority Data

Jun. 20, 1989 [IT] Italy .............................. MI 20917A/89

[51] Int. Cl.$^6$ ................................................... C07C 41/01
[52] U.S. Cl. ........................... 568/677; 568/684; 570/135
[58] Field of Search .................... 568/677, 683, 568/685, 615; 570/135, 142

[56] References Cited

U.S. PATENT DOCUMENTS

| | | | |
|---|---|---|---|
| 3,684,786 | 8/1972 | Chandrasekaran | 526/89 |
| 3,896,167 | 7/1975 | Sianesi et al. | 562/849 |
| 3,962,348 | 6/1976 | Benninger et al. | 568/677 |
| 3,985,810 | 10/1976 | Halasz et al. | 568/615 |
| 4,077,857 | 3/1978 | Toy et al. | 204/157.92 |
| 4,149,016 | 4/1979 | Toy et al. | 568/664 |
| 4,321,359 | 3/1982 | Toy et al. | 568/665 |
| 4,523,039 | 6/1985 | Logow et al. | 568/615 |
| 4,533,762 | 8/1985 | Campbell et al. | 568/677 |
| 4,568,478 | 2/1986 | Middleton et al. | 252/187.2 |
| 4,577,044 | 3/1986 | Campbell et al. | 568/677 |
| 4,588,796 | 5/1986 | Wheland | 526/214 |
| 4,597,882 | 7/1986 | Nishimura et al. | 508/111 |
| 4,782,130 | 11/1988 | Re et al. | 528/70 |
| 4,898,991 | 2/1990 | Huang | 568/615 |
| 4,900,872 | 2/1990 | Guglielmo et al. | 568/684 |
| 4,947,006 | 8/1990 | Marraccini et al. | 568/685 |
| 4,990,283 | 2/1991 | Visca et al. | 252/309 |
| 5,013,472 | 5/1991 | Marracinni et al. | |
| 5,087,765 | 2/1992 | Marraccini et al. | 568/677 |

FOREIGN PATENT DOCUMENTS

| | | | |
|---|---|---|---|
| 321990A | 6/0000 | European Pat. Off. | C07C 43/12 |
| 267627A | 5/1988 | European Pat. Off. | C07C 43/12 |
| 2148286 | 5/1985 | United Kingdom . | |

OTHER PUBLICATIONS

K.K. Johri et al., J. Org. Chem. 1983, 48, 242–250.

*Primary Examiner*—Gary Geist
*Assistant Examiner*—Sreeni Padmanabhan
*Attorney, Agent, or Firm*—Nakaido, Marmelstein, Murray & Oram LLP

[57] ABSTRACT

The invention relates to a process for preparing perhaloethers from perhaloolefins and to a few "per se" new classes of perhaloethers thereby obtained.

The process consists in reacting a perhalomonoolefin with a fluoroxy compound $R_x$—OF (wherein $R_x$ represents a perhalogenated alkyl radical) at a temperature not exceeding 20° C. in a liquid reaction medium and in the presence of inert gases.

7 Claims, No Drawings

PROCESS FOR PREPARING PERHALOETHERS FROM PERHALOOLEFINS AND NEW PERHALOETHERS THEREBY OBTAINED

This is a division of application Ser. No. 08/352,440, filed Dec. 9, 1994, Pat. No. 5,648,560, which is a continuation application of Ser. No. 08/283,614, abandoned, filed Aug. 1, 1994, which is a continuation of Ser. No. 08/038, 188, filed Mar. 29, 1993, abandoned, which is a continuation of Ser. No. 07/722,408, filed Jun. 20, 1991 abandoned, which is a CIP of Ser. No. 07/540,639 filed Jun. 19, 1990, abandoned.

DESCRIPTION OF THE INVENTION

The present invention relates to a process for preparing perhaloether compounds starting from perhaloolefins.

In particular, the present invention relates to a process for preparing perhalomonoethers and perhalopolyethers having defined structure and molecular weight, by reacting at least a perhaloolefin with at least a fluoroxy compound. The invention relates also to new perhaloethers obtained by the aforesaid process.

The obtained compounds are used in particular in the fields of the electric insulating liquids, of the lubricants and of the heat transmission means.

Processes for preparing fluorinated polyethers by fluorination of substrates or of hydrogenated polymers and rupture of the polymeric chain are known in the art (U.S. Pat. No. 4,523,039). This type of process involves long operative times, of the order of a few days, to obtain a complete fluorination.

On the other hand it is known (U.S. Pat. No. 3,962,348) to obtain perlfluoropolyethers from fluoroolefins and hydrogenated polyols and subsequent electrofluorination. Also in this case the process requires very long reaction times and, in addition, the use of HF involves several technological, safety problems etc.

There are also processes for preparing mixtures of perfluoropolyethers having not defined molecular weights and determinable as average molecular weight of the terms contained in the mixtures, on the basis of the ethereal units present in the chains, by photo-oxidation or polymerization of perfluoroolefins. In this case too the processes in question are complicated and at any rate alien to the one which is the object of the present invention.

Lastly, it is known how to prepare perfluoromonoethers by addition reaction of $CF_3OF$ on olefins, carried out for example by using stoichiometric amounts of the reactants at low temperatures and in the presence of ultraviolet light (U.S. Pat. Nos. 4,077,857 and 4,149,016), or in the gas phase at high temperatures (from 20° to 175° C.) (Int. J. Chem. Kinet. 1984, 1612, 103–115). There are obtained, following modalities different from the ones forming the object of the present invention, exclusively monoethereal addition products other than the ones being the object of the present invention.

It is known too (J. Org. Chem. 1985, 50, 3698–3701 that the use of complex oxidative mixtures consisting of perfluoroacylipofluorites in combination with mono- and bisfluoroxy compounds, produced in situ in an aqueous medium, and utilized as liquids under pressure as starters for the polymerization of perfluorinated monomers, leads to the obtainment of solid polymeric materials having a very high molecular weight.

The Applicant has now surprisingly found a simple and economic method for preparing perhaloethers endowed with defined structure and molecular weight, which is not affected by the drawbacks illustrated in connection with the above-discussed prior art.

It was found, in fact, that by reacting a perhalomonoolefin with a fluoroxy compound, better defined hereinafter, in certain temperature and dilution conditions in an inert gas, it is possible to obtain perhaloether compounds exhibiting a strictly delimited structure and molecular weight.

A portion of said perhaloether compounds is per se new and represents a further surprising feature of the intrinsic novelty of the process object of the present invention.

Thus, it is an object of the present invention to provide a simple and economic process for preparing perhaloethers (mono- and poly-ethers) with ether end groups, having a structure and molecular weight selectively restricted falling within the defined limits of a low oligomerization.

Another object is to provide the abovesaid perhaloethers also in the form of a directly useful mixture.

Lastly, still another object is to provide "per se" new perhaloethers or mixtures thereof.

These and still further objects, which will be better apparent to those skilled in the art from the following description, are achieved, according to the present invention, by means of a process for preparing perhaloethers, which is characterized in that at least a perhalomonoolefin is reacted with at least a fluoroxy compound $R_x$—OF, wherein $R_x$ represents a straight or branched perhaloalkyl radical containing from 1 to 10 carbon atoms, at a temperature not higher than 20° C., in the presence of a gas which is inert to the reaction conditions.

In the present specification, fluoroxy compound $R_x$—OF will be also referred to as "starter".

Furthermore, the term "perhalomonoolefin" defines monoolefins, in which all the hydrogen atoms have been substituted by atoms of chlorine and fluorine, or of fluorine.

As regards fluoroxy compound $R_x$—OF, the halogen component can be Cl, F, Br, I, preferably it is selected from F and Cl or F.

Accordingly, it is possible to use all the perhalomonoolefins compatible with the above-described process.

For illustrative purposes, and in consideration of the applicative purposes of the obtained products, there are usually utilized one or more perfluorinated and/or fluorochlorinated perhalomonolefins and/or mixtures thereof selected from perfluoromonoolefins, fluorochloromonoolefins, perfluoroalkylvinylethers and mixtures thereof, defined as follows:

1) one or more perfluoromonoolefins;
2) a fluorochloromonoolefin in combination with a perfluoroalkylvinylether and/or another perfluoromonoolefin;
3) one or more perfluoroalkylvinylethers;
4) a perfluoromonoolefin in combination with a perfluoroalkylvinylether.

Preferably, fluoroxy compound $R_x$—OF contains from 1 to 3 carbon atoms, furthermore, the halogen component is selected from chlorine and fluorine, even better, it consists of fluorine.

As regards the perhalomonoolefins, they preferably contain from 2 to 6 carbon atoms, the halogen component of which being selected, as mentioned hereinbefore, from F and Cl, or fluorine.

It resulted to be advantageous to use, among the perfluoromonoolefins, perfluoropropene and tetrafluoroethylene and, among the fluorochloromonoolefins, chlorotrifluoroethylene and 1,2-dichloro-difluoroethylene. Last, as regards the perfluoroalkylvinylethers, they are corresponding to the following formula:

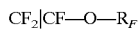

wherein $R_F$ represents a straight or branched perfluoroalkyl radical containing from 1 to 10 and preferably from 1 to 3 carbon atoms, such as perfluoromethylvinylether, perfluoroethylvinylether or perfluoropropylvinylether.

According to a preferred embodiment, the process of the present invention is carried out in a liquid phase, which consists of an inert organic medium and/or of one or more perhalomonoolefins, with a gaseous stream consisting of the starter or of the starter mixture, an inert gas stream and, optionally, a gaseous or liquid stream consisting of the perhalomonolefinic reactant or of mixtures thereof, the last-mentioned stream being always present, if the liquid phase does not contain perhalomonoolefins prior to the reaction starting.

Preferably, the inert gas is fed to the liquid phase in admixture with the gaseous stream consisting of the starter or of its mixtures, is determined quantitative ratios, and it is preferably selected from nitrogen, helium, argon, $CF_4$ and $C_2F_6$ and mixtures thereof.

The inert organic solvent medium, when used, consists of a straight or cyclic fluorocarbon or chlorofluorocarbon. $CFCl_3$; $CF_2Cl_2$; c.$C_4F_8$; $CF_3$—$CF_2Cl$; $CF_2Cl$—$CFCl_2$ and $CF_2Cl$—$CF_2Cl$ have proved to be suitable solvents.

Preferably, the liquid phase is composed of one or more perhalomonoolefins.

The starter $R_x$—OF or its mixtures can be utilized in association with miner amounts of starter fluorine ranging from 1 to 30% by mols, preferably from 5 to 20% by mols with respect to $R_x$—OF.

Analogous results are obtainable also by operating in a fully gaseous phase.

The ether products, in which A=B=F in formulas II–IV, as defined hereinafter, can be selectively obtained also by using only elemental fluorine diluted with the inert gas, in the same conditions as already described.

As mentioned before, the reaction temperature shall be lower than 20° C., and exactly; the minimum temperature at which the liquid phase is maintained during the reaction shall be such that the component or components of said phase remain in the liquid state. The reaction temperature can range, on the whole, from −120° C., to +20° C., approximately, and usually it is maintained approximately from −100° C. to −30° C. The total pressure is generally maintained around the ambient values (about 1 atmosphere).

The gaseous volume ratio of the starter or starters to the inert gas can vary over a wide range, for example from 0.01 to 5.

The concentration of the perhalomonoolefin or of its mixtures in the liquid phase usually ranges from 0.01 to 10 moles/liter of total liquid phase, higher values being allowable up to the molar concentration of the perhalomonoolefin and mixtures thereof in the pure state.

The feeding of the starter or of its mixtures in the gas phase is adjusted in such a way as to keep its flourate rate ranging from 0.01 to 5 moles per hour per one liter of liquid phase and usually it ranges from 0.05 to 2 moles per hour per liter of liquid phase.

When tetrafluoroethylene is utilized as a perhalomonoolefin, this is preferaly fed in the gaseous state by bubbling it into the liquid phase of the solvent and/or of another liquid perhaloolefin.

At the end of the adjusted reaction time, which is usually comprised between approximately 2 and 20 hours, the perhaloether products, which are obtained, in mixture, are separated by distillation from the unreacted perhaloolefin monomer or monomers and from the solvent, if any. In such manner, mixtures of perhaloether products are obtained, which have the appearance of colorless transparent liquids.

A further separation of the components or of—narrower cuts of mixtures, starting from the mixtures of the obtained perhaloether products can be carried out by fractionated distillation, gas-chromatographic techniques, etc., thereby obtaining products or product cuts having a narrow range, for example, of the boiling points or an analogous boiling point (isomeric mixtures, etc.).

The reaction can be conducted in a completely continuous manner, by continuously with drawing a liquid phase portion from the reactor, subjecting said portion to distillation and recycling the solvent, if any, and the unreacted monomer or monomers and separating the reaction product.

As mentioned before, the reaction product consists of a mixture of monoperhaloethers or of perhalopolyethers and optionally of minor amounts of perhaloalkanes, depending on the type of the starting perhalomonoolefin or of mixtures thereof and depending on the utilized starter or starters. Said mixtures, in most of cases, can be used directly without further separation treatments, etc.

Hereinafter are described in particular a few embodiments of the process object of the present invention and the obtained products or mixtures thereof, a few of said products being new "per se" and are intended for being included in the scope of the present invention.

I) When a perfluoromonoolefin having at least three carbon atoms and, as a starter, a fluoroxy compound $R_x$—OF either alone or associated with elemental fluorine are used, the obtained products have the following formula:

wherein

A is like or different from B and consists of $R_xO$; $R_yO$; $R_y$; F;

$R_f$ represents a straight or branched perfluoroalkyl radical containing from 1 to 10 carbon atoms and preferably from 1 to 3 carbon atoms;

$R_y$ represents a straight or branched perhaloalkyl radical containing at least 1 carbon atom less than $R_x$, and l is 1 or 2;

$R_f$ preferably represents $CF_3$ and $R_y$=$CF_3$ and/or —$CF_2$—$CF_3$.

The products having formula I, in which l=2 and A and B are not $R_y$ or F simultaneously, are new "per se".

In particular, when the starting perhalomonoolefin is perfluoropropene alone and the starter consists of a fluoroxy compound as defined above either alone or in admixture with fluorine, the following products are obtained, in which M represents the monomeric unit derived from perfluoropropene:

| | |
|---|---|
| F—(M)₁—F | (A) |
| R$_x$O—(M)₁—F | (B) |
| R$_x$O—(M)₁—OR$_x$ | (C) |
| R$_y$—(M)₁—F | (D) |
| R$_y$—(M)₁—OR$_x$ | (E) |
| R$_y$O—(M)₁—F | (F) |
| R$_x$O—(M)₁—OR$_y$ | (G) |
| R$_y$—(M)₁—R$_y$ | (H) | wherein R$_x$ and R$_y$ are the same as defined above. The products B, C, E, F and G for 1–2 are new "per se".

In the case under examination, the starting perfluoromonoolefin is perfluoropropene and the monomeric unit M represents, therefore, a diradical

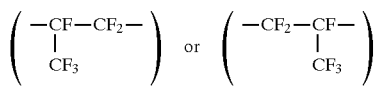

wherefore to products A–H, for example to product (B) for 1=1, two specific isomeric products correspond, which have respectively the formulas:

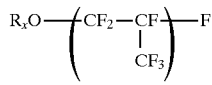

and

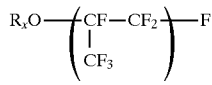

and furthermore for 1=2, all the combinations between the isomeric monomeric units are possible, wherefore, for example, always in the case of the product of formula (B), four specific products having the following formulas can be present:

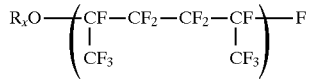

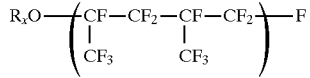

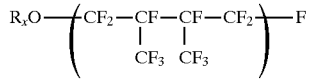

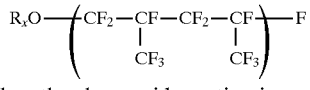

When the abovesaid reaction is carried out with elemental F$_2$ only, the perfluoroalkane products (A), known "per se", where 1=1 and 2, are selectively obtained.

The obtained perhaloether mixtures can contain, generally in little amounts, also products different from the ones indicated, for example due to the re-arrangement of the monomeric unit or units, under such reaction conditions as to promote local exothermicities.

For example, when it is operated with perfluoropropene alone or in combination, monomeric units of the type

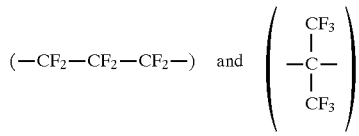

can be present.

Therefore, when perfluoropropene is reacted, as above mentioned, with CF$_3$OF and with elemental F$_2$, the mixture A–H of the obtained products is composed in particular of:

| | | |
|---|---|---|
| CF$_3$—CF(CF$_3$)—CF$_3$ | (1) | 1 = 1 |
| CF$_3$—CF$_2$—CF$_2$—CF$_3$ | (2) | 1 = 1 |
| CF$_3$—CF$_2$—CF(CF$_3$)—CF$_3$ | (3) | 1 = 1 |
| CF$_3$—CF$_2$—CF$_2$—CF$_2$—CF$_3$ | (4) | 1 = 1 |
| CF$_3$O—CF(CF$_3$)—CF$_3$ | (5) | 1 = 1 |
| CF$_3$O—CF$_2$—CF$_2$—CF$_3$ | (6) | 1 = 1 |
| CF$_3$—CF(CF$_3$)—CF(CF$_3$)—CF$_3$ | (7) | 1 = 2 |
| CF$_3$—CF(CF$_3$)—CF$_2$—CF$_2$—CF$_3$ | (8) | 1 = 2 |
| CF$_3$(CF$_2$)$_4$CF$_3$ | (9) | 1 = 2 |
| CF$_3$—CF(CF$_3$)—(CF$_2$)$_3$CF$_3$ | (10) | 1 = 2 |
| CF$_3$—(CF$_2$)$_2$—C(CF$_3$)$_2$ | (11) | 1 = 2 |
| CF$_3$O—(CF$_2$)$_3$—CF(CF$_3$)$_2$ | (12) | 1 = 2 |
| CF$_3$O—CF$_2$—CF(CF$_3$)—CF(CF$_3$)—CF$_3$ | (13) | 1 = 2 |
| CF$_3$O—CF(CF$_3$)—CF$_2$—CF(CF$_3$)—CF$_3$ | (14) | 1 = 2 |
| CF$_3$O—CF$_2$CF(CF$_3$)—(CF$_2$)$_2$—CF$_3$ | (15) | 1 = 2 |
| CF$_3$O—CF(CF$_3$)—(CF$_2$)$_3$CF$_3$ | (16) | 1 = 2 |
| CF$_3$O—(CF$_2$)$_6$—CF$_3$ | (17) | 1 = 2 |
| CF$_3$O—CF$_2$—CF(CF$_3$)—CF(CF$_3$)—CF$_2$—OCF$_3$ | (18) | 1 = 2 |
| CF$_3$O—CF$_2$—CF(CF$_3$)—CF$_2$—CF(CF$_3$)—OCF$_3$ | (19) | 1 = 2 |
| CF$_3$O—CF(CF$_3$)—CF$_2$)$_2$—CF(CF$_3$)—OCF$_3$ | (20) | 1 = 2 |
| CF$_3$O—CF(CF$_3$)—(CF$_2$)$_4$—OCF$_3$ | (21) | 1 = 2 |

Products (11), (12) and (21) are characterized by a re-arrangement of the monomeric unit and the products from (12) to (21), belonging to series A–H, are "per se" new.

Furthermore, the dimeric products (1=2) can represent up to 90% and above of the obtained products, of which the mono- and bis-ether products can represent even more than 60%.

When the abovesaid reaction is conducted at rather high temperatures, for example at about −30° C., with a high CF$_3$OF/inert gas volume ratio, for example >5, ether products, prevailingly consisting of products (12), (13), (17), (18), (20) and (21), are present in the mixture.

Conversely, when the abovesaid volume ratio is of about 0.25, the ether products present in the mixture prevailingly consist of products (13)–(16) and (18)–(20).

When perfluoropropene is reacted with C$_2$F$_5$OF or with a mixture of C$_2$F$_5$OF and elemental fluorine, the mixture of the obtained products is almost exclusively composed of:

| | | |
|---|---|---|
| CF$_3$—CF(CF$_3$)—CF(CF$_3$)—CF$_3$ | (7) | 1 = 2 |
| CF$_3$—CF(CF$_3$)—CF$_2$—CF$_2$—CF$_3$ | (8) | 1 = 2 |
| CF$_3$—(CF$_2$)$_4$—CF$_3$ | (9) | 1 = 2 |
| CF$_3$—CF(CF$_3$)—(CF$_2$)$_3$—CF$_3$ | (10) | 1 = 2 |
| C$_2$F$_5$—O—CF(CF$_3$)$_2$ | (1A) | 1 = 1 |
| C$_2$F$_5$O—CF$_2$—CF$_2$—CF$_3$ | (2A) | 1 = 1 |
| CF$_3$O—CF$_2$—CF(CF$_3$)—(CF$_2$)$_2$—CF$_3$ | (3A) | 1 = 2 |
| CF$_3$O—CF(CF$_3$)—(CF$_2$)$_3$—CF$_3$ | (4A) | 1 = 2 |
| C$_2$F$_5$O—(CF$_2$)$_3$—CF(CF$_3$)$_2$ | (5A) | 1 = 2 |
| C$_2$F$_5$O—CF(CF$_3$)—CF$_2$—CF(CF$_3$)$_2$ | (6A) | 1 = 2 |
| C$_2$F$_5$O—CF$_2$CF(CF$_3$)—CF(CF$_3$)$_2$ | (7A) | 1 = 2 |
| C$_2$F$_5$O—CF$_2$CF(CF$_3$)—(CF$_2$)$_2$—CF$_3$ | (8A) | 1 = 2 |
| C$_2$F$_5$O—CF(CF$_3$)—(CF$_2$)$_3$—CF$_3$ | (9A) | 1 = 2 |
| C$_2$F$_5$O—CF$_2$CF(CF$_3$)—CF(CF$_3$)CF$_2$CF$_3$ | (10A) | 1 = 2 |
| C$_2$F$_5$O—CF$_2$—CF(CF$_3$)—CF$_2$—CF(CF$_3$)$_2$ | (11A) | 1 = 2 |
| C$_2$F$_5$O—CF(CF$_3$)—(CF$_2$)$_2$—CF(CF$_3$)$_2$ | (12A) | 1 = 2 |
| C$_2$F$_5$O—CF(CF$_3$)—CF$_2$—CF(CF$_3$)—CF$_2$—CF$_3$ | (13A) | 1 = 2 |
| C$_2$F$_5$O—CF$_2$CF(CF$_3$)—CF$_2$—CF(CF$_3$)—OC$_2$F$_5$ | (14A) | 1 = 2 |
| C$_2$F$_5$O—CF$_2$—CF(CF$_3$)—CF(CF$_3$)—CF$_2$—OC$_2$H$_5$ | (15A) | 1 = 2 |
| C$_2$F$_5$O—CF(CF$_3$)—(CF$_2$)$_2$—CF(CF$_3$)—OC$_2$F$_5$ | (16A) | 1 = 2 |

The products from (3A) to (16A) are new "per se".
Product (5A) derives from a re-arrangement of the monomeric unit.

(II) When a perfluoroalkylvinylether having formula:

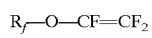

wherein $R_f$ is the same as defined hereinbefore, is used as a starting monoolefin, the resulting products have the general formula:

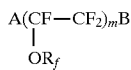  (II)

wherein $R_f$ represents a perfluoroalkyl radical containing from 1 to 10 and preferably from 1 to 3 carbon atoms, as defined before, and m=1 or 2.

The products having formula II where m=2 are "per se" new.

When a perfluoroalkylvinylether alone is used as a starting perfluoromonoolefin and a fluoroxy compound either alone or in admixture with elemental fluorine is used as a starter, the following products, wherein letter N represents the monomeric unit, are obtained:

| | |
|---|---|
| F—(N)$_m$—F | (A') |
| R$_x$O—(N)$_m$—F | (B') |
| R$_x$O—(N)$_m$—OR$_x$ | (C') |
| R$_y$—(N)$_m$—F | (D') |
| R$_y$—(N)$_m$—OR$_x$ | (E') |
| R$_y$O—(N)$_m$—F | (F') |
| R$_x$O—(N)$_m$—OR$_y$ | (G') |
| R$_y$—(N)$_m$—R$_y$ | (H') | wherein $R_x$, $R_y$ are the same as defined hereinbefore.

In the indicated formulae of products A'–H', (H) represents a diradical

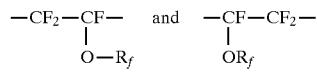

so that, analogously with what discussed above in relation to the reaction with perfluoropropene, two specific products correspond to each formula A'–H' where m=1, and four specific products correspond to each formula A'–H' where m=2.

When it is operated with perfluoroalkylvinylethers alone or in combination, monomeric units, caused by a re-arrangement, of the type

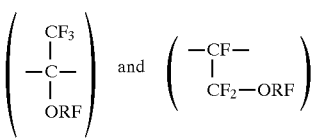

wherein $R_f$ is the same as defined before, can be present.

When the abovesaid reaction is carried out with elemental fluorine, only the ether products of formula (A'), where m=1 and 2, are obtained.

When perfluoromethylvinylether $CF_3O$—$CF$=$CF_2$ is reacted with $CF_3OF$ either alone or in admixture with elemental $F_2$, the mixture of the obtained products is almost exclusively composed of:

| | | |
|---|---|---|
| $CF_3$—$CF(OCF_3)$—$CF(OCF_3)$—$CF_3$ | (1a) | m = 2 |
| $CF_3$—$CF(OCF_3)$—$CF_2$—$CF_2$—$OCF_3$ | (2a) | m = 2 |
| $CF_3O$—$(CF_2)_4$—$OCF_3$ | (3a) | m = 2 |
| $CF_3O$—$CF(OCF_3)$—$CF_3$ | (4a) | m = 1 |
| $CF_3O$—$CF_2$—$CF_2$—$OCF_3$ | (5a) | m = 1 |
| $CF_3O$—$CF(OCF_3)$—$CF_2$—$CF(OCF_3)$—$CF_3$ | (6a) | m = 2 |
| $CF_3O$—$CF(OCF_3)$—$(CF_2)_3$—$OCF_3$ | (7a) | m = 2 |
| $CF_3O$—$CF_2$—$CF(OCF_3)$—$CF(OCF_3)$—$CF_3$ | (8a) | m = 2 |
| $CF_3O$—$CF_2$—$CF(OCF_3)$—$(CF_2)_2$—$OCF_3$ | (9a) | m = 2 |
| $CF_3O$—$CF(OCF_3)$—$CF_2$—$CF(OCF_3)$—$CF_2$—$OCF_3$ | (10a) | m = 2 |
| $CF_3O$—$CF(OCF_3)$—$(CF_2)_2$—$CF(OCF_3)$—$OCF_3$ | (11a) | m = 2 |
| $CF_3O$—$CF_2$—$CF(OCF_3)$—$CF(OCF_3)$—$CF_2$—$OCF_3$ | (12a) | m = 2 |

These products, with the exception of (5a), are new "per se".

When perfluoromethylvinylether is reacted with $C_2F_5OF$ alone or in admixture with elemental fluorine, the mixture of the obtained products is composed of:

| | | |
|---|---|---|
| $CF_3$—$CF(OCF_3)$—$CF_3$ | (5) | m = 1 |
| $CF_3$—$CF_2$—$CF_2$—O—$CF_3$ | (6) | m = 1 |
| $C_2F_5O$—$CF(OCF_3)$—$CF_3$ | (3c) | m = 1 |
| $C_2F_5O$—$(CF_2)_2OCF_3$ | (4c) | m = 1 |
| $CF_3$—$CF(OCF_3)$—$CF(OCF_3)$—$CF_3$ | (1a) | m = 2 |
| $CF_3$—$CF(OCF_3)$—$(CF_2)_2$—$OCF_3$ | (2a) | m = 2 |
| $CF_3O(CF_2)_4$—$OCF_3$ | (3a) | m = 2 |
| $C_2F_5O$—$CF_2$—$CF(OCF_3)CF_3$ | (5c) | m = 2 |
| $C_2F_5O$—$CF(OCF_3)$—$CF_2$—$CF_3$ | (6c) | m = 2 |
| $CF_3$—$CF(OCF_3)$—$(CF_2)_3$—$OCF_3$ | (7c) | m = 2 |
| $CF_3$—$CF(OCF_3)$—$CF_2$—$CF(OCF_3)$—$CF_3$ | (8c) | m = 2 |
| $CF_3$—$CF_2$—$CF(OCF_3)$—$CF(OCF_3)$—$CF_3$ | (9c) | m = 2 |
| $CF_3$—$CF_2$—$CF(OCF_3)$—$CF_2$—$CF_2$—O—$CF_3$ | (10c) | m = 2 |
| $C_2F_5O$—$CF(OCF_3)$—$(CF_2)_3$—$OCF_3$ | (11c) | m = 2 |
| $C_2F_5O$—$CF(OCF_3)$—$CF_2$—$CF(OCF_3)$—$CF_3$ | (12c) | m = 2 |
| $C_2F_5O$—$CF_2$—$CF(OCF_3)$—$CF(OCF_3)$—$CF_3$ | (13c) | m = 2 |
| $C_2F_5O$—$CF_2$—$CF(OCF_3)$—$(CF_2)_2$—$OCF_3$ | (14c) | m = 2 |
| $C_2F_5O$—$CF(OCF_3)$—$CF_2$—$CF(OCF_3)$—$CF_2$—O—$C_2F_5$ | (15c) | m = 2 |
| $C_2F_5O$—$CF(OCF_3)$—$(CF_2)_2$—$CF(OCF_3)$—O—$C_2F_5$ | (16c) | m = 2 |
| $C_2F_5O$—$CF_2$—$CF(OCF_3)$—$CF(OCF_3)$—$CF_2$—O—$C_2F_5$ | (17c) | m = 2 |
| $C_2F_5$—$C(CF_3)(OCF_3)$—$CF(CF_3)$—$OCF_3$ | (18c) | m = 2 |
| $CF_3CF(OCF_3)$—$CF(OC_2F_5)$—$CF_2$—$OCF_3$ | (19c) | m = 2 |

The products, with the exception of (5), (6), (4c), are new "per se". Products (18c) and (19c) are characterized by a re-arrangement in the monomeric unit.

When perfluoropropylvinylether is reacted with $C_2F_5OF$ alone or in admixture with elemental fluorine, in the product mixture the following new products are present:

| | |
|---|---|
| $C_3F_7$—O—$CF(CF_3)$—O—$C_2F_5$ | (1d) |
| $C_3F_7$—O—$CF_2$—$CF_2$—O—$C_2F_5$ | (2d) |
| $C_3F_7$—O—$CF(CF_3)$—$CF(CF_3)$—O—$C_3F_7$ | (3d) |
| $C_3F_7$—O—$CF(CF_3)$—$CF_2$—$CF_2$—O—$C_3F_7$ | (4d) |
| $C_3F_7$—O—$(CF_2)_4$—O—$C_3F_7$ | (5d) |
| $C_2F_5OCF_2CF(OC_3F_7)(CF_2)_2OC_3F_7$ | (6d) |
| $C_2F_5OCF(OC_3F_7)(CF_2)_3OC_3F_7$ | (7d) |

When perfluoroethylvinylether $C_2F_5$—O—$CF$=$CF_2$ is reacted with $CF_3OF$, the resulting mixture prevailingly contains the following new products:

| | |
|---|---|
| $CF_3$—$CF(OC_2F_5)$—$CF(OC_2F_5)$—$CF_3$ | (1b) |
| $CF_3$—$CF(OC_2F_5)$—$(CF_2)_2$—$OC_2F_5$ | (2b) |
| $C_2F_5O$—$(CF_2)_4$—$OC_2F_5$ | (3b) | besides (14c), (15c), (16c) and (17c).

The new products (1a), (2a) and (3a); (1b), (2b) and (3b; (1c), (2c) and (3c); (3d), (4d) and (5d), have been furthermore selectively obtained by reacting the respective perfluoroalkylvinylethers with elemental fluorine.

III) When a mixture of a perfluoroalkylvinylether and a perfluoroolefin is utilized as starting monoolefins, the products of formula:

$$A(CF_2—CF)_m(CF—CF_2)_lB \atop \phantom{A(}OR_f\phantom{)_m(}X \qquad (III)$$

are obtained, wherein

A, B and $R_f$ are the same as defined hereinbefore, m is 0, 1, 2; 1=0, 1, 2 such that m+1=2, x represents a fluorine atom or a radical $R_f$, with $R_f$ being the same as defined before.

Preferably, x=F or $CF_3$.

The products with m=1=1 are new "per se".

Analogously with what has been considered before, the monomeric units are enchained with one another according to any possible combinations.

When the abovesaid mixture consists of $R_fO$—$CF$=$CF_2$ and perfluoropropene, the following new products are obtained, in which M represents the perfluoropropene monomeric unit and N the one of $R_fO$—$CF$=$CF_2$:

| | |
|---|---|
| F(M)(N)F | (A") |
| $R_xO(M)(N)F$ | (B") |
| $R_xO(M)(N)OR_x$ | (C") |
| $R_y(M)(N)F$ | (D") |
| $R_y(M)(N)OR_x$ | (E") |
| $R_yO(M)(N)F$ | (F") |
| $R_xO(M)(N)OR_y$ | (G") |
| $R_y(M)(N)R_y$ | (H") | besides the products A–H and A'–H'.

When $CF_3$—O—$CF$=$CF_2$ is reacted with perfluoropropene by using $CF_3OF$ either alone or in combination with elemental fluorine, the resulting mixture contains, besides the new compounds (1a), (2a), (3a), (13), (15), (16), (19), the new compounds:

| | |
|---|---|
| $CF_3O$—$CF_2$—$CF_2$—$CF(CF_3)_2$ | (1e) |
| $CF_3O$—$(CF_2)_4CF_3$ | (2e) |
| $CF_3O$—$CF(CF_3)$—$(CF_2)_2$—$CF_3$ | (3e) |
| $CF_3O$—$CF(CF_3)$—$CF(CF_3)$—$CF_3$ | (4e) |
| $CF_3O$—$CF_2$—$CF(OCF_3)$—$CF_2$—$CF_2$—$CF_3$ | (5e) |
| $CF_3O$—$CF(OCF_3)$—$CF_2$—$CF(CF_3)_2$ | (6e) |
| $CF_3O$—$CF_2$—$CF(OCF_3)$—$CF_2$—$CF(CF_3)$—$OCF_3$ | (7e) |
| $CF_3O$—$CF_2$—$CF(OCF_3)$—$CF(CF_3)$—$CF_2$—$OCF_3$ | (8e) |

When $CF_3O$—$CF$=$CF_2$ is reacted with tetrafluoroethylene by using $CF_3OF$ either alone or in combination with elemental fluorine, the resulting mixture contains the new compounds (1a), (2a), (3a), (7a), (9a) and

| | |
|---|---|
| $CF_3O$—$CF(CF_3)$—$CF_2$—$CF_3$ | (1f) |
| $CF_3O$—$(CF_2)_3$—$CF_3$ | (2f) |
| $CF_3O$—$CF_2$—$CF(OCF_3)$—$CF_2$—$CF_3$ | (3f) |
| $CF_3O$—$CF(OCF_3)$—$(CF_2)_3CF_3$ | (4f) |
| $CF_3O(CF_2)_4OCF_3$ | (5f) |
| $CF_3O(CF_2)_2$—$CF(CF_3)OCF_3$ | (6f) |

The new products (1f), (2f), (1e), (2e), (3e), (4e) are selectively obtained also by reacting the abovesaid mixtures with elemental fluorine.

(IV) When a mixture of a perfluoroalkylvinylether and a chlorofluoroolefin selected from CFCl=CFCl and $CF_2$=CFCl is utilized as starting monoolefins, the products of formula:

$$A(CF_2—CF)_m(CF—CFCl)_nB \atop \phantom{A(}OR_f\phantom{)_m(}Y \qquad (IV)$$

are obtained, wherein

A, B and $R_f$ are the same as defined before and m=0, 1, 2; n=0, 1, 2 so that m+n=2;

Y represents an atom of F or Cl.

The products with m=n=1 are new "per se".

Analogously with what has been discussed before, the monomeric units are enchained with each other according to any possible combinations.

When the abovesaid mixture is composed of $R_fOCF$=$CF_2$ and CFCl=CFCl, the following new products are obtained, in which N represents the monomeric unit of $R_f$—O—$CF$=$CF_2$ and L the one of CFCl=CFCl:

| | |
|---|---|
| F(N)(L)F | (A''') |
| $R_xO(N)(L)F$ | (B''') |
| $R_xO(N)(L)OR_x$ | (C''') |
| $R_y(N)(L)F$ | (D''') |
| $R_y(N)(L)OR_x$ | (E''') |
| $R_yO(N)(L)F$ | (F''') |
| $R_xO(N)(L)OR_y$ | (G''') |
| $R_y(N)(L)R_y$ | (H''') | besides products A'–H'.

When $CF_3O$—$CF$=$CF_2$ is reacted with CFCl=CFCl using $CF_3OF$ alone or in combination with fluorine, the mixture of obtained products contains the following new products (1a), (2a), (3a) and

| | |
|---|---|
| $CF_3$—$CF(OCF_3)$—CFCl—$CF_2Cl$ | (1g) |
| $CF_3O$—$(CF_2)_2$—CFCl—$CF_2Cl$ | (2g) |
| $CF_3O$—$CF_2$—$CF(OCF_3)$—CFCl—$CF_2Cl$ | (3g) |

-continued

| | |
|---|---|
| CF$_3$O—CF$_2$—CF(OCF$_3$)—CFCl—CFCl—OCF$_3$ | (4g) |
| CF$_3$O—CF(OCF$_3$)—CF$_2$—(CFCl)$_2$—OCF$_3$ | (5g) |

When in the abovesaid reaction CF$_2$=CFCl is used as a chlorofluoroolefin, the mixture of obtained products contains the following new products (1a), (2a), (3a) and

| | |
|---|---|
| CF$_3$O—CF(CF$_3$)—CFCl—CF$_3$ | (1h) |
| CF$_3$O—(CF$_2$)$_2$—CFCl—CF$_3$ | (2h) |
| CF$_3$O—(CF$_2$)$_2$—CF$_2$—CF$_2$Cl | (3h) |
| CF$_3$O—CF(CF$_3$)—CF$_2$CF$_2$Cl | (4h) |
| CF$_3$O—CF(CF$_3$)—CFCl—CF$_2$—OCF$_3$ | (5h) |
| CF$_3$O(CF$_2$)$_2$—CFCl—CF$_2$OCF$_3$ | (6h) |

Products (1g), (2g), (1h)–(4h) were also obtained selectively by reacting the abovesaid mixtures of olefins with elemental fluorine.

The process forming the object of the present invention permits to achieve several advantages, which can be briefly indicated as the possibility of obtaining perhaloethers having defined structure and molecular weight, by means of a simple and flexible process, operating on the concerned parameters, such as the choice of the perhalomonoolefin and of the fluoroxy starter compound, in a single reaction step.

The art has not offered so far such a possibility.

The perhalogenated products which contain fluorine and chlorine, prepared by means of the process of the present invention, have an important applicative field as electric insulating materials, lubricants and heat transmission media.

The perfluorinated ethers of the invention are compounds, which are well known for their exceptional thermal stability, thermooxidative stability and stability to chemical agents as well as for their uninflammability properties and are utilizable in very different sectors and under extremely severe operative conditions.

The perfluoropolyethers known in the art generally consist of mixtures of products, from which it is difficult to obtain the individual compounds. Reference should be made in this connection to GB patent 1,226,556. The perfluoropolyethers of the present invention are generally obtainable as isomeric mixtures of compounds having their boiling points in a very narrow temperature range.

The perfluoropolyethers of the invention are particularly useful as fluids for the testing in electronics, for example for the leak testing, thermal shock testing, hot spot location, dew point determination and the like.

The polyethers containing bromine and/or iodine atoms are utilized as intermediates for the preparation of functionalized derivatives.

The following examples are given for merely illustrative purposes and are not to be regarded as limitative of any possible embodiment of the process.

EXAMPLE 1

218 g of C$_3$F$_6$ were condensed in a glass reactor having a volume of 500 ml, equipped with a stirrer, thermometer, gas feeding pipes reaching the reactor bottom, and with cooler with a liquid at −78° C. connected to the atmosphere.

Subsequently, while maintaining an outer cooling such as to keep the inner temperature at −40° C., a flow of 2.0 N1/h of CF$_3$OF and 1 N1/h of N$_2$ was fed during 14 hours by bubbling into the liquid phase.

260 g of a rough reaction product were obtained, from which, after having distilled off the unreacted C$_3$F$_6$ and the volatile by-products, 52 g of a limpid and colorless liquid were obtained, which, analyzed by means of gas mass in electronic impact with 1% SP-1100 column and FT-NMR spectrometry for $^{19}$F, resulted to be composed of products 1 to 21, the content of dimeric 12 to 21) (1=2) monoether (12–17) and bisether (18–21) products, thereof determined by gas-chromatography, amounted to about 55% by weight of the mixture the bisether dimers/monoether dimers weight ratio being of 1 to 2.

The dimeric monoether products (12–17) have boiling point in the temperature range of −91°±2° C. at atmospheric pressure.

The dimeric bisether products have boiling point in the temperature range of −121°±2° C.

Ether products (12), (17) and (21) were present in traces.

EXAMPLE 2

Example 1 was repeated according to the same modalities, using 2.8 N1/h of CF$_3$OF diluted with 0.5 N1/h of N$_2$ bubbled into 186 g of C$_3$F$_6$ maintained at −40° C.

The products obtained, after removal of C$_3$F$_6$, were the same as in example 1. The ether terms (12), (13), (17), (18) and (21) represented about 90% of the dimeric ether products obtained. The ether terms (12), (17) and (21) were characterized by a re-arrangement of the monomeric unit.

EXAMPLE 3

By operating according to the modalities described in example 1, a flow of 1 N1/h of C$_2$F$_5$OF and 0.2 N1/h of F$_2$ diluted with 5 N1/h of N$_2$ was bubbled for 11.5 hours into 233 g of C$_3$F$_6$ kept in liquid phase at −48° C.

There were obtained 214 g of a rough reaction mixture which, after C$_3$F$_6$ removal, was analyzed by means of gas-chromatography, gas-mass and $^{19}$F NMR; it resulted to be composed of products 1A to 16A. Products 3A to 16A represented about 20% of the mixture. The dimeric monoether products (3A–13A) were in a weight ratio of about 1:1 with respect to the dimeric bisether products (14A–16A).

EXAMPLE 4

Into a steel AISI 316 tubular reactor having an inside diameter of ⅛ inch and a length of 1 m, equipped with a circulating-liquid cooling jacket, maintained at −10° C. and downstream connected with a trap maintained at −80° C., a flow of 2 N1/h of gaseous C$_3$F$_6$ diluted with 10 N1/h of N$_2$ and a flow of 1 N1/h of CF$_3$OF diluted with 10 N1/h of N$_2$ were simultaneously and separately fed during 2 hours by means of a two-way inlet connection.

The resulting reaction products leaving the reactor and condensed in the trap, after removal of C$_3$F$_6$, of the perfluoroalkane dimers and of the monomeric monoethers (1=1), were analyzed by means of the above-cited techniques; they resulted to be composed of dimeric monoethers and diethers (12)–(21), the weight ratio being 5:1.

EXAMPLE 5

By operating according to the procedure described in example, 1, 1 N1/h of CF$_3$OF diluted with 3 N1/h of N$_2$ was bubbled into 230 g of C$_3$F$_6$ in the liquid state at −60° C. and was reacted for 19 hours.

After removal of C$_3$F$_6$ and of the other products which had formed (1–11), the dimeric monoethers and diethers (1=2) were in a ratio of about 1:1.

EXAMPLE 6

By operating according to the procedure described in example 1, a flow of 1 N1/h of CF$_3$OF diluted with 5 N1/h of $N_2$ was bubbled for 6 hours into 200 g of $CF_3O$—$CF=CF_2$ kept in the liquid state at $-60°$ C.

190 g of a rough reaction mixture were obtained, from which, by means of distillation, 45 g of ether products consisting of (1a)–(12a) were recovered.

EXAMPLE 7

Example 6 was repeated, by bubbling for 12 hours a flow of 1 Nl/h of $F_2$ diluted with 50 Nl/h of $N_2$, into 186 g of $CF_3O$—$OF=CF_2$ maintained at $-97°$ C.

185 g of a rought reaction mixture were obtained, from which, after removal of the unreacted $CF_3O$—$CF=CF_2$ and of the volatile by-products, 81 g of dimeric bis ether products (1a), (2a) and (3a), which boil at about $60°$ C.$±2°$ C. were obtained.

EXAMPLE 8

By operating according to the modalities of example 1, after bubbling a flow of 1.5 Nl/h of $C_2F_5OF$ diluted with 7.5 Nl/h of $N_2$ into 200 g of $CF_3O$—$CF=CF_2$ in the liquid state at $-50°$ C., during 6 hours, 200 g of a rough reaction mixture were obtained, from which, by distillation, 58 g of ether products were recovered; these products, subjected to the analyses, resulted to be composed of products (1a), (2a), (3a), (5), (6) and from 3c) to (19c) in the following weight ratio: tetraethers/triethers/diethers=1/3/6.5.

Products (18c) and 19c) were present in little amounts.

EXAMPLE 9

By operating according to the modalities described in example 1, after bubbling of 0.75 Nl/h of $C_2F_5OF$ and of 0.75 Nl/h of $F_2$ diluted with 60 Nl/h of $N_2$ into 112 g of $C_3F_7$—O—$CF=CF_2$ in the liquid state at $-50°$ C., during 5 hours, 127.5 g of a rough reaction mixture were obtained, which was composed for 65% of products (1d)–(7d) and in which the products (3d)–(5d) represented 20%.

EXAMPLE 10

Example 9 was repeated by bubbling a flow of 1 Nl/h of $F_2$ diluted with 70 Nl/h of $N_2$ during 6 hours into 178 g of $C_3F_7$—O—$CF=CF_2$ in the liquid state at $-75°$ C.: 177 g of a rough reaction product were obtained, from which, by distillation, 65 g of bis-ether products (1d), (2d) and (3d), which boil at about $120°$ C.$±2°$ C., were separated.

EXAMPLE 11

By operating according to the modalities described in example 1, after bubbling a flow of 1 Nl/h of $CF_3OF$ diluted with 3 Nl/h of $N_2$, during 6 hours, into 200 g of $C_2F_5$—O—$CF=CF_2$ in the liquid state at $-60°$ C., after removal of the unreacted monomer and of the volatile by-products, a mixture was obtained containing bisether products (1b)–(3b) and (14c)–(17c).

EXAMPLE 12

By operating according to the modalities described in example 1, after bubbling, during 13 hours, a flow of 1 Nl/h of $F_2$ diluted with 50 Nl/h of $N_2$ into 225 g of (liquid $C_2F_5O$—$CF=CF_2$ maintained at $-75°$ C., 180 g of a rough reaction product were obtained, which consisted by 66% of dimeric diethers (1b), (2b) and (3b), which boil at about $98°$ C.$±2°$ C.

EXAMPLE 13

By operating according to the modalities described in example 1, after bubbling, during 6 hours, a flow of 2 Nl/h of $CF_3OF$ diluted with 5 Nl/h of $N_2$ into a liquid phase maintained at $-60°$ C. and composed of 115 g of $CF_3O$—$CF=CF_2$ and of 105 g of $C_3F_6$, after removal of the unreacted monomers and of the volatile by-products, a mixture was obtained containing products (1a)–(3a), (13), (15), (16), (19) and (1e)–(8e).

EXAMPLE 14

Example 13 was repeated by bubbling, for 6 hours, a flow of 1.5 Nl/h of $F_2$ diluted with 50 Nl/h of $N_2$ into 116.2 g of $CF_3O$—$CF=CF_2$ and 105 g of $C_3F_6$ at $-100°$ C.; after removal of the unreacted monomers and of the volatile by-products, 74 g of products consisting of (1a)–(3a) (63.5%), (7)–(9) (11.4%) and (1e)–(4e) (24.7%) were obtained.

EXAMPLE 15

By operating according to the modalities described in example 1, after bubbling, during 5 hour, a flow of 1 Nl/h of $CF_3OF$ diluted with 3 Nl/h of $N_2$ and, simultaneously but separately, a flow of 3 Nl/h of gaseous $C_2F_4$ into 106 g of liquid $CF_3O$—$CF=CF_2$ maintained at $-75°$ C., after removal of the unreacted monomers and of the volatile by-products, a mixture containing products (1a)–(3a), (7a), (9a) and (1f)–(6f) was obtained.

EXAMPLE 16

Example 15 was repeated by bubbling, during 5 hours, a flow of 1 Nl/h of $F_2$ diluted with 50 Nl/h of $N_2$ into the same liquid phase at $-100°$ C. with the same flow of $C_2F_4$; after the separation, 31.5 g of dimeric products consisting of 52% of (1f) and 2f) and by 48% of (1a)–(3a) were obtained.

EXAMPLE 17

By operating according to the modalities described in example 1 and after bubbling for 5 hours 1.5 Nl/h of $CF_3OF$ diluted with 2 Nl/h of $N_2$ into liquid 55 g of $CF_3O$—$CF=CF_2$ and 42 g of $CFCl=CFCl$ maintained at $-65°$ C., after removal of the unreacted monomers and of the volatile by-products, a mixture was obtained, which contained products (1a)–(3a) and (1g)–(5g).

EXAMPLE 18

Example 17 was repeated by bubbling, during 5 hours, a flow of 1.5 Nl/h of $F_2$ diluted with 80 Nl/h of $N_2$ into the same liquid phase at $-100°$ C., there were obtained by distillation 43.4 g of dimeric products consisting by 28% of products (1a)–(3a), by 26% of products (3 g) and by 46% of products (1 g) and 2 g).

EXAMPLE 19

By operating according to the modalities described in example 1 and after bubbling, during 5 hours, 1.2 Nl/h of $CF_3OF$ diluted with 3 Nl/h of $N_2$ into 80 liquid g of $CF_3O$—$CF=CF_2$ and 57 g of $CF_2=CFCl$, maintained at $-70°$ C., after removal of the unreacted monomers, a mixture was obtained containing products (1h)–(6H) besides (1a)–(3a).

EXAMPLE 20

Example 19 was repeated by bubbling, during 5 hours a flow of 1.2 Nl/h of $F_2$ diluted with 60 Nl/h of $N_2$ into the same liquid phase maintained at $-100°$ C., there were obtained, after separation, products (1a)–(3a) and (1h)–(4h), the latter products representing 41% of the obtained mixture.

EXAMPLE 21

By operating according to the modalities described in example 1 and after bubbling, during 14 hours, 0.5 Nl/h of $CF_3OF$ diluted with 2 Nl/h of $N_2$ into a liquid phase consisting of 50 g of $CF_2Cl$—$CF_2Cl$ and of 54.7 g of $C_3F_6$, there were obtained, after removal of the volatile by-products, 8.5 g of a product consisting of (5)–(10), (13)–(16) and (18)–(20).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. New perhaloethers having formula:

  (I)

wherein A the same or different from B, represents $R_xO$, $R_yO$, $R_y$, and F, provided that A and B are not simultaneously $R_y$ or F;

$R_f$ represents a straight or branched perfluoroalkyl radical containing 1 to 10 carbon atoms;

$R_x$ represents a straight or branched perhaloalkyl radical containing 1 to 10 carbon atoms;

$R_y$ represents a straight or branched perhaloalkyl radical, having the meaning as defined for $R_x$ with at least a carbon atom less.

2. New perhaloethers having formula (I), as defined in claim 1, wherein $R_f$=$CF_3$ and $R_y$=$CF_3$ or —$CF_2$—$CF_3$.

3. New perhaloethers having formula:

  (II)

wherein A, B and $R_f$ are the same as defined in claim 1.

4. New perhaloethers having formula:

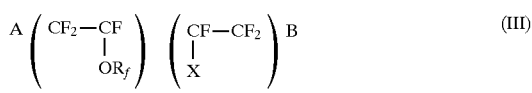  (III)

wherein A, B and $R_f$ are the same as defined in claim 1, X represents a fluorine atom or $R_f$.

5. New perhaloethers according to claim 4, in which X=$CF_3$.

6. Perhaloethers having the formula:

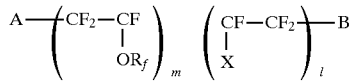

wherein A and B are the same or different and A and B represent $R_xO$, $R_yO$, $R_y$, and F, provided that A and B are not simultaneously $R_y$ or F;

$R_x$ represents a straight or branched perhaloalkyl radical containing from 1 to 10 carbon atoms;

$R_y$ represents a straight or branched perhaloalkyl radical, having the meaning as defined for $R_x$ with at least one less carbon atom; and $R_f$ represents a perfluoroalkyl radical containing 1 to 10 carbon atoms, X represents a fluorine atom or $R_f$; and m=l=1.

7. Perhaloethers having the formula:

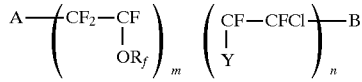

wherein A and B are the same or different and A and B represent $R_xO$, $R_yO$, $R_y$, and F, provided that A and B are not simultaneously $R_y$ or F; $R_x$ represents a straight or branched perhaloalkyl radical containing from 1 to 10 carbon atoms; $R_y$ represents a straight or branched perhaloalkyl radical, having the meaning as defined for $R_x$ with at least one less carbon atom; and $R_f$ represents a perfluoroalkyl radical containing 1 to 10 carbon atoms, Y represents a fluorine or chlorine atom; and m=n=1.

* * * * *